US011179302B2

(12) United States Patent
Dardelle

(10) Patent No.: US 11,179,302 B2
(45) Date of Patent: Nov. 23, 2021

(54) CORE-COMPOSITE SHELL MICROCAPSULES

(71) Applicant: Firmenich SA, Geneva (CH)

(72) Inventor: Gregory Dardelle, Geneva (CH)

(73) Assignee: Firmenich SA, Satigny (CH)

( * ) Notice: Subject to any disclaimer, the term of this patent is extended or adjusted under 35 U.S.C. 154(b) by 150 days.

(21) Appl. No.: 16/311,365

(22) PCT Filed: Jun. 29, 2017

(86) PCT No.: PCT/EP2017/066116
§ 371 (c)(1),
(2) Date: Dec. 19, 2018

(87) PCT Pub. No.: WO2018/002214
PCT Pub. Date: Jan. 4, 2018

(65) Prior Publication Data
US 2019/0240124 A1  Aug. 8, 2019

(30) Foreign Application Priority Data
Jun. 30, 2016  (EP) .................................... 16177050

(51) Int. Cl.
*A61K 8/11* (2006.01)
*A61K 8/88* (2006.01)
*A61K 8/65* (2006.01)
*B01J 13/16* (2006.01)
*B01J 13/14* (2006.01)
*C11D 3/50* (2006.01)
*B01J 13/12* (2006.01)
*B01J 13/10* (2006.01)
*B01J 13/20* (2006.01)
*A61Q 5/12* (2006.01)
*A61K 8/84* (2006.01)
*A61Q 19/10* (2006.01)
*A61Q 13/00* (2006.01)
*A61K 8/40* (2006.01)
*A61K 8/73* (2006.01)
*A61Q 15/00* (2006.01)
*A61K 8/87* (2006.01)
*A61K 8/9789* (2017.01)

(52) U.S. Cl.
CPC ................. *A61K 8/11* (2013.01); *A61K 8/40* (2013.01); *A61K 8/65* (2013.01); *A61K 8/73* (2013.01); *A61K 8/731* (2013.01); *A61K 8/737* (2013.01); *A61K 8/84* (2013.01); *A61K 8/87* (2013.01); *A61K 8/88* (2013.01); *A61K 8/9789* (2017.08); *A61Q 5/12* (2013.01); *A61Q 13/00* (2013.01); *A61Q 15/00* (2013.01); *A61Q 19/10* (2013.01); *B01J 13/10* (2013.01); *B01J 13/12* (2013.01); *B01J 13/14* (2013.01); *B01J 13/16* (2013.01); *B01J 13/206* (2013.01); *C11D 3/505* (2013.01); *A61K 2800/654* (2013.01)

(58) Field of Classification Search
CPC ... A61K 8/11; A61K 8/40; A61K 8/65; A61K 8/73; A61K 8/731; A61K 8/737; A61K 8/84; A61K 8/87; A61K 8/88; A61K 8/9789; A61K 2800/654; A61Q 13/00; A61Q 15/00; A61Q 19/10; A61Q 5/12; B01J 13/10; B01J 13/12; B01J 13/14; B01J 13/16; B01J 13/206; C11D 3/505
See application file for complete search history.

(56) References Cited

U.S. PATENT DOCUMENTS

| 3,551,346 A | 12/1970 | Breen et al. |
| 3,897,361 A | 7/1975 | Saeki et al. |
| 4,137,180 A | 1/1979 | Naik et al. |
| 5,180,637 A | 1/1993 | Sumii |
| 5,236,615 A | 8/1993 | Trinh et al. |
| 8,242,069 B2 * | 8/2012 | Struillou .................. A61K 8/11 510/441 |
| 2005/0112152 A1 | 5/2005 | Popplewell et al. |

FOREIGN PATENT DOCUMENTS

| EP | 799885 A | 10/1997 |
| GB | 1141186 A | 1/1969 |
| GB | 1257178 A | 12/1971 |
| JP | 2012512933 A | 6/2012 |
| WO | 1997034986 A1 | 9/1997 |
| WO | 2014044840 A1 | 3/2014 |
| WO | WO-2015041791 A1 * | 3/2015 ......... C11D 17/0039 |
| WO | 2016071150 A1 | 5/2016 |

OTHER PUBLICATIONS

International Search Report and Written Opinion, application PCT/EP2017/066116, dated Jun. 29, 2017.
Fan et al., Material Science Forum, 2011, vol. 675-677, p. 1109-1112.
Parker A. et al., Soft Matter 2010, 6, p. 4916-4919.
Ullmann's Encyclopedia of Industrial Chemistry, vol. A08, p. 315-448.
Ullmann's Encyclopedia of Industrial Chemistry, vol. A25, p. 747-817.

* cited by examiner

*Primary Examiner* — Irina S Zemel
(74) *Attorney, Agent, or Firm* — Armstrong Teasdale LLP

(57) ABSTRACT

The invention relates to a method for making a core-composite shell microcapsule slurry for the delivery of hydrophobic active ingredients such as fragrance components of perfume oils. The method includes forming an outer shell by coacervation surrounding an internal phase which contains the hydrophobic active ingredient; and forming an inner shell by interfacial polymerization at the interface between the internal phase and the outer shell. The internal phase contains the hydrophobic active ingredient. The microcapsules are typically incorporated in a consumer product wherein the composite shell prevents the hydrophobic active ingredient from release until desired, generally during use of the consumer product.

17 Claims, 2 Drawing Sheets

US 11,179,302 B2

CORE-COMPOSITE SHELL MICROCAPSULES

FIELD OF THE INVENTION

The invention relates to a delivery system comprising both a core and a composite shell formed by a coacervate and synthetic polymer, and the use of the delivery system for encapsulating a liquid, a solid, an emulsion or a dispersion containing a hydrophobic active ingredient such as a perfume or a flavor oil.

BACKGROUND OF THE INVENTION

Perfume additives make consumer products such as home and body care products, and in particular laundry compositions, more aesthetically pleasing to the consumer and in many cases the perfume imparts a pleasant fragrance to fabrics treated therewith. The amount of perfume carryover from an aqueous laundry bath onto fabrics, however, is often marginal. By encapsulating perfume additives in microcapsules, the delivery efficiency and active lifetime of the perfume additives can be improved. Microcapsules provide several advantages, such as protecting the perfume from physical or chemical reactions with incompatible ingredients in the laundry composition, as well as protecting the perfume from volatilization or evaporation. Microcapsules can be particularly effective in the delivery and preservation of perfumes in that the perfumes can be delivered to and retained within the fabric by a microcapsule that only ruptures, and therefore releases the perfume, when the fabric is dry. The rupture of microcapsules can be induced by various factors such as temperature so that the contents are delivered when the capsule degrades. Alternatively the microcapsules can be compromised by physical forces, such as crushing, or other methods that compromise the integrity of the microcapsules. Additionally, the microcapsule contents may be delivered via diffusion through the capsule wall during a desired time interval.

Scent associated with laundered laundry is important to many consumers. There are many so called "touch points" that consumers associate with during the laundry experience. Non-limiting examples of these touch points include the freshness experience associated with opening a fabric care container, opening a washing machine after washing laundry, opening a laundry dryer after drying laundry, and freshness associated with wearing laundered clothes. It has been reported that there is a significant portion of consumers that will fold and put away their laundry about one day after having laundered laundry. Freshness while folding laundry about one day after having laundered laundry also signals to the consumer that the laundry is clean.

Personal and body care products constitute other categories of goods for which the consumer experience vis-à-vis the perfume is very important, and perfume delivery systems are necessary to provide the benefit expected from consumers such as a perfume blooming during use or yet a long lasting effect.

Multilayered capsules are known in the art. US 2005/0112152 generally describes encapsulated fragrance further coated with a second coating, such as a cationic coating. British patent application GB 1257178 discloses multi-coated capsules produced by forming a secondary film layer at the interfaces of hydrophilic and hydrophobic liquids in the defective parts of the already formed primary film layer, e.g., crackles, capillary micropores or the like present therein, to fill up the defects.

British patent application GB 1141186 discloses dual walled capsules produced by first precoating droplets or solid particles of an internal phase in an aqueous vehicle through an interfacial reaction between two reactants, one of which is present in the aqueous vehicle, the other being present in or on the internal phase; and then providing another coating by coacervation.

U.S. Pat. No. 5,180,637 describes double-walled microcapsules wherein the primary wall is composed of an amino resin prepared by polycondensation reaction and the secondary wall is formed by coacervation of a polyion complex of the resin with polystyrenesulfonic acid or salt thereof, whereby liquid droplets are deposited on the primary wall. While those microcapsules are said to have improved resistance to heat and moisture, the structure of the shell consisting of superposed distinct layers is likely to delaminate and provide products which are still highly permeable.

Fan et al. reports preparing microcapsules with triallylamine-containing core surrounded by polyelectrolyte shell of controlled thickness via layer-by-layer assembly technology ("Preparation of oil core/multilayerpolyelectrolyte shell microcapsules by a coacervation method," Materials Science Forum (2011), vol. 675-677 (Pt. 2, Adv. Mat. Science and Technology), p. 1109-1112).

WO2014044840 discloses a method of making multilayer core/shell microcapsules for delivery of active agents such as fragrance components of perfume oils. The method includes forming an outer shell by coacervation surrounding an internal phase which contains the active agent; and forming an inner shell by interfacial polymerization at the interface between the internal phase and the outer shell. In this document, the polymerization reaction requires the presence of a reactant since said polymerization reaction is induced between an isocyanate and a reactant (in particular, a diamine or a polyol) to obtain a polyurea polymer.

Although multilayered capsules are generally known in the art, the quality of these capsules and/or the way to manufacture them could be improved. Thus, there is a need in the industry for microcapsules with improved barrier and release properties for encapsulated materials prepared by simplified and cost-effective processes. The present invention satisfies this and other needs of the industry.

SUMMARY OF THE INVENTION

It has now been found that performing microcapsules encapsulating a hydrophobic active ingredient such as a perfume oil could be obtained by forming a composite wall formed from the polymerisation of a polyisocyanate in absence of a reactant such as an amine or polyamine into the existing coacervate shell. Unexpectedly, even with very limited amounts of such polyisocyanate used, those capsules demonstrate a high performance in terms of stability.

In a first aspect, the present invention relates to a process for making a core-composite shell microcapsule slurry, which comprises:
(i) providing as a dispersion in an aqueous vehicle, a hydrophobic internal phase comprising at least one polyisocyanate having at least three isocyanate functional groups and a hydrophobic active ingredient;
(ii) mixing a first and second polyelectrolytes in the aqueous vehicle under conditions sufficient to form a suspension of complex coacervate nodules;
(iii) depositing the complex coacervate nodules at an interface of the aqueous vehicle adjacent to the hydrophobic internal phase to form an outer shell of microcapsule, wherein the hydrophobic internal phase forms the core and contains the polyisocyanate and the hydrophobic active ingredient therein; and (iv) providing conditions sufficient to induce interfacial polymerization of the polyisocyanate inside the outer shell to form an inner shell at the interface between the internal phase and the outer shell to form a core-composite shell microcapsule slurry, characterized in that no amine or polyamine susceptible to polymerize with the polyisocyanate to form the inner shell is added at any stage of the process.

In a second aspect, the present invention relates to core-composite shell microcapsules comprising an outer shell of a coacervate, an inner shell consisting essentially of polymerised polyisocyanate formed from at least one polyisocyanate comprising at least three isocyanate functional groups in the absence of a reactant consisting of a polyamine or an amine, and an internal phase comprising a hydrophobic active ingredient, wherein the inner shell and outer shell form a composite structure.

In a third aspect, the present invention relates to the use of core-composite shell microcapsules disclosed herein as a perfuming composition for consumer products. These consumer products are generally in the form of a home- or personal-care product that includes the microcapsules therein, and are preferably in liquid or powder form specifically as a detergent composition, a fabric softener, a hard surface cleaning composition, or a dishwashing composition, or a shampoo, a hair conditioner, a shower or bath mousse, oil or gel, a deodorant, or an antiperspirant.

DETAILED DESCRIPTION OF THE INVENTION

Figure 1:
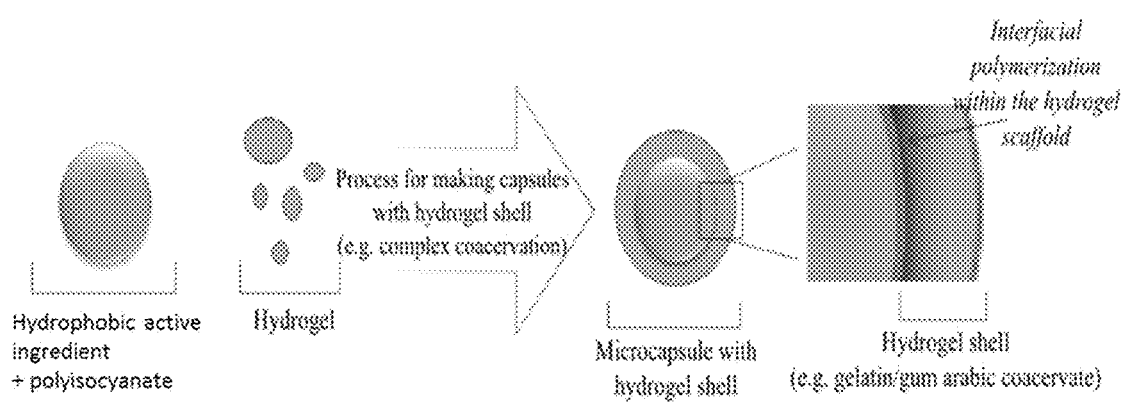
FIG. 1 is a diagram showing a process for making the core-composite shell microcapsules of the invention.

Unless otherwise specified, % are meant to designate percentages by weight of a composition.

According to the invention, "no amine or polyamine susceptible to polymerize with the polyisocyanate to form the inner shell" means that, if present, the amount of amine or polyamine added has to be sufficiently low so as not to be able to significantly change the properties of the microcapsule wall if it reacts with the polyisocyanate. Typically, the amount of amine functionalities that can be added in the process of the present invention is less than 50% molar, preferably less than 25% molar, most preferably less than 10% molar of the amount of isocyanate functionalities.

According to a particular embodiment, no amine or polyamine susceptible to polymerize with the polyisocyanate to form the inner shell is added between step (iii) and step (iv).

According to a particular embodiment, the process is completely free from an addition of amine or polyamine susceptible to polymerize with the polyisocyanate to form the inner shell.

According to the invention, by "no amine or polyamine susceptible to polymerize with the polyisocyanate is added at any stage of the process to form the inner shell", it should be understood that the inner shell is formed only due to the autopolymerization of the polyisocyanate that occurs during the interfacial polymerization.

In other words, first and second polyelectrolytes that act in the formation of the outer shell are therefore excluded from the definition "no amine or polyamine susceptible to polymerize with the polyisocyanate to form the inner shell is added at any stage of the process".

According to the invention, a "core-composite shell microcapsule" refers to a microcapsule comprising a composite shell having two interlinked layers, it is meant a shell consisting of layers that are linked by chemical or physical interactions, thereby forming one composite structure.

As physical or chemical interactions, one may cite covalent bonds, ionic bonds, coordinate covalent bonds, hydrogen bonds, van der Waals interaction, hydrophobic interactions, chelation, or steric effects.

The present invention relates to a simplified and cost-effective process to prepare composite core-shell microcapsules having dual wall shells of a hydrogel/polyurea composite structure. It has been found that even in the absence of a water-soluble reactant such as an amine or a polyamine reacting with a polyisocyanate to form said synthetic polymer, capsules with equivalent or better performance than those known heretofore could be obtained. This is surprising as the presence of an amine or polyol as water-soluble reactant for the polyisocyante was disclosed in the prior art as essential to prepare such composite membrane with required properties. The process of the present invention provides membrane compositions and particular structure which have shown to provide benefits notably in terms of stability.

In the present invention, two processes are combined, namely, a complex coacervation process (forming an outer hydrogel shell) and an interfacial polymerization process without the presence of an amine (forming an inner polymeric shell) to obtain core/composite shell capsules having good properties. Without being bound by theory, it is believed that the coacervate constituting the outer shell of the microcapsule acts as a scaffold for the polymerization of the inner polymer shell. Such combination results in the formation of a composite membrane with two interlinked layers. By composite membrane with two interlinked layers, it is meant a membrane consisting of layers that are linked by chemical and physical interactions, thereby forming one inseparable entity. The structure is therefore such that the outer coacervate is linked to the inner polymer shell. Such composite membranes with interlinked layers remain interlinked even upon mechanical breakage, therefore they undergo breakage as a whole (rather than delaminating or breaking one layer after the other).

Thus, by conducting both the complex coacervation and interfacial polymerization processes within the same process unit without adding a reactant to induce the interfacial polymerization, the method of the present invention advantageously reduces the process time and cost while also providing capsules that exhibit the desired properties.

As a first object, the invention relates to a process for making a core-composite shell microcapsule slurry, which comprises:

(i) providing as a dispersion in an aqueous vehicle, a hydrophobic internal phase comprising at least one polyisocyanate having at least three isocyanate functional groups and a hydrophobic active ingredient;

(ii) mixing a first and second polyelectrolytes in the aqueous vehicle under conditions sufficient to form a suspension of complex coacervate nodules;

(iii) depositing the complex coacervate nodules at an interface of the aqueous vehicle adjacent to the hydrophobic internal phase to form an outer shell of microcapsule, wherein the hydrophobic internal phase forms the core and contains the polyisocyanate and the hydrophobic active ingredient therein; and (iv) providing conditions sufficient to induce interfacial polymerization of the polyisocyanate inside the outer shell to form an inner shell at the interface between the internal phase and the outer shell to form a core-composite shell microcapsule slurry, characterized in that no amine or polyamine susceptible to polymerize with the polyisocyanate to form the inner shell is added at any stage of the process.

According to a particular embodiment, no amine or polyamine selected from the group consisting of guanidine salts, tris-(2-aminoethyl)amine, N,N,N',N'-tetrakis(3-aminopropyl)-1,4-butanediamine, guanazole, lysine is added at any stage of the process.

According to an embodiment, no substantial amount of other water-soluble reactant than amine or polyamine susceptible to polymerize with the polyisocyanate is added at any stage of the process, said water-soluble reactant being chosen in the group consisting of polyols, thiols, ureas, urethanes and mixtures thereof.

A typical process for making the microcapsule of the present invention comprises the following steps and is schematized in FIG. 1.

Formation of the Outer Hydrogel Shell by Complex Coacervation

Two oppositely charged polyelectrolytes are mixed under specific temperature, pH and concentration conditions to induce polymer phase separation, so as to produce a suspension of complex coacervate nodules. The person skilled in the art will be able to select the optimal conditions (pH, conditions) according to the nature of the polyelectrolytes. The complex coacervate nodules have to deposit at the active interface to form core-shell capsules. Optionally, the capsules undergo a chemical or enzymatic cross-linking step. Furthermore, the hydrophobic active agent to be encapsulated, typically a fragrancing material such as a perfume oil, must already contain the appropriate polyisocyanate which is polymerized to form the inner shell.

Formation of the Inner Shell by Polymerization at the Coacervate/Oil Interface

According to the invention, the polymerization of the polyisocyanate contained within the core of the capsule is induced without requiring the addition of any amine or polyamine in the aqueous vehicle.

Indeed, it has been thus found that, a polyisocyanate comprising at least three isocyanate functional groups—preferably aromatics—even present in limited amount in the hydrophobic internal phase was capable of polymerisation with sufficient efficiency to provide a capsule wall with good properties.

Without being bound by theory, it is believed that, due to the high reactivity of the polyisocyanate, a polymerization of the polyisocyanate present in the internal phase occurs at the beginning of the process as soon as the internal phase (oil phase) and the aqueous vehicle (aqueous phase) are mixed and over time, thereby reducing the process time.

According to an embodiment, the polymerization of the polyisocyanate is carried out under the same conditions (pH, temperature) as the ones for the formation of the coacervate.

However, the temperature and/or the pH may also be adjusted during the process to control the rate of interfacial polymerization.

According to a particular embodiment, the pH of the microcapsule slurry obtained in step (iv) is not adjusted above 7 to preserve the structure of the shell.

Indeed, under alkaline pH, the coacervate constituting the hydrogel shell can solubilize leading to the disruption of the shell and finally to disintegration of the structure of the microcapsule.

According to an embodiment, the pH of the solution(s) during the whole process is equal or below 7.

Without being bound by theory, it is believed that, the coacervate or hydrogel shell acts as a scaffold upon which the polyisocyanate may be polymerized thereby forming the inner polyurea shell.

The microcapsules of the invention are made from the following ingredients:
(a) a first polyelectrolyte (Polyelectrolyte I)
(b) a second polyelectrolyte (Polyelectrolyte II)
(c) one polyisocyanate having at least three isocyanate functional groups
(d) a hydrophobic active agent encapsulated within the microcapsules (a) A first polyelectrolyte (Polyelectrolyte I) of one charge, preferably selected among proteins that are able to interact with an electrolyte or polyelectrolyte that has an opposite charge to thus form a coacervate phase having the ability to coat hydrophobic interfaces in order to form the capsules. In a preferred embodiment, Polyelectrolyte I is positively charged for pH<8 so as to form gels or highly viscous solutions in water below the gelling temperature, and lower viscosity solutions in water at a temperature above the melting point of the gel. The viscosity above the gelling temperature is typically lower than 0.1 Pa·s; below the gelling temperature, the elastic modulus G' of the gel is typically in the range 0.1-15 kPa when measured during the first 24 hours after gel formation, using the measurement methods based on shear rheometry (such methods, along with the definitions relevant for the gelling temperature, are described, for example, in Parker, A. and Normand, V., *Soft Matter*, 6, pp 4916-4919 (2010). Preferably, Polyelectrolyte I is a gelatin material.

(b) A second polyelectrolyte (Polyelectrolyte II), which is preferably selected among polysaccharides or another polymer bearing charges of opposite polarity compared to Polyelectrolyte I. Generally, Polyelectrolyte II is negatively charged for pH >2. Preferably, Polyelectrolyte II is a polyelectrolyte that is only weakly negatively charged at pH >2; such polyelectrolytes are, for example, carboxymethyl cellulose, sodium carboxymethyl guar gum, or xanthan gum, or yet plant gums such as acacia gum. Most preferably, it is acacia gum (gum arabic). The ratio between polyelectrolyte 1 and polyelectrolyte 2 is preferably comprised between 10/0.1 to 0.1/10.

According to an embodiment, the first polyelectrolyte carries a net positive charge when the pH is less than 8 while the second polyelectrolyte carries a net negative charge when the pH is greater than 2.

According to an embodiment, the first polyelectrolyte is gelatin and the second polyelectrolyte is selected from the group consisting of caboxymethyl cellulose, sodium caboxymethyl guar gum, xanthan gum and plant gums.

According to a preferred embodiment, the first polyelectrolyte is gelatin and the second is acacia gum.

(c) Suitable polyisocyanates used according to the invention include aromatic polyisocyanate, aliphatic polyisocyanate and mixtures thereof. According to the invention, the internal phase comprises at least one polyisocyanate having at least 3 but may comprise up to 6, or even only 4, isocyanate functional groups.

According to a particular embodiment, a triisocyanate (3 isocyanate functional groups) is used.

According to an embodiment, a mixture of a diisocyanate (2 isocyanate functional groups) with a triisocyanate (3 isocyanate functional groups) is used.

According to a particular embodiment, the hydrophobic internal phase is essentially free from diisocyanate.

According to a particular embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, said at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

According to an embodiment, the at least one polyisocyanate used in the process of the invention is present in amounts representing preferably from 0.1 to 30 wt %, preferably 0.5 to 15 wt %, more preferably from 1 to 10 wt % and even more preferably from 2 to 8 wt % of the hydrophobic internal phase.

The skilled person in the art will be able to choose a suitable amount of polyisocyanate according to the nature of the desired application.

According to a particular embodiment, the hydrophobic internal phase essentially consists of the hydrophobic active ingredient with the at least one polyisocyanate having at least three isocyanate functional groups.

The volume of the inner shell typically represents 0.1 to 99%, preferably 0.1 to 80% of the total volume of the shell.

(d) By "hydrophophic active ingredient", it is meant any active ingredient—single ingredient or a mixture of ingredients—which forms a two-phases solution in water.

Hydrophobic active ingredients are preferably chosen from the group consisting of flavor, flavor ingredients, perfume, perfume ingredients, nutraceuticals, cosmetics, insect control agents, biocide actives and mixtures thereof.

The nature and type of the insect control agents present in the hydrophobic internal phase do not warrant a more detailed description here, which in any case would not be exhaustive, the skilled person being able to select them on the basis of its general knowledge and according to intended use or application.

Examples of such insect control agents are birch, DEET (N,N-diethyl-m-toluamide), essential oil of the lemon *eucalyptus* (Corymbia *citriodora*) and its active compound p-menthane-3,8-diol (PMD), icaridin (hydroxyethyl isobutyl piperidine carboxylate), Nepelactone, Citronella oil, Neem oil, Bog Myrtle (*Myrica* Gale), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the hydrophobic internal phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

The process according to the invention can comprise a further step of drying the slurry obtained in step (iv) to obtain dried core-composite shell microcapsules.

A core-composite shell microcapsule slurry or core-composite shell microcapsule obtainable by a process as defined in any of the above-embodiment, wherein the inner shell consists essentially of polymerised polyisocyanate formed from at least one polyisocyanate comprising at least three isocyanate functional groups in the absence of a reactant consisting of a polyamine or an amine is another object of the invention. By "essentially", it should be understood that the amount of amine or polyamine present in the inner shell is sufficiently low so as not to be able to significantly change the properties of the microcapsule wall if it reacts with the polyisocyanate.

Another object of the present invention is core-composite shell microcapsules comprising an outer shell of a coacervate, an inner shell consisting essentially of polymerised polyisocyanate formed from at least one polyisocyanate comprising at least three isocyanate functional groups in the absence of a reactant consisting of a polyamine or an amine, and an internal phase comprising an hydrophobic active ingredient, wherein the inner and outer shell form a composite structure.

Microcapsules according to the invention, although prepared with a simplified process, and in particular in the absence of a reactant being an amine or a polyamine to polymerise with the polyisocyanate, are showing equivalent or better performance in particular in terms of stability compared to capsules prepared with a similar process but in the presence of an amine or polyamine.

The microcapsule of the present invention is a core/composite-shell system comprising a membrane which typically contains gelatin, gum arabic and water; and an internal phase which contains polyisocyanate and the hydrophobic active ingredient (for example a perfume oil).

Typically, the microcapsules of the invention have a mean core radius size of between 1 µm and 5,000 µm, preferably between 5 µm and 1,000 µm. Microcapsules having a mean core radius size between 100 µm and 500 µm have proved useful in certain body care products. In other cases, microcapsules wherein the mean core radius size was between 10 and 40 µm also proved to be useful. The size of the microcapsules can be easily adjusted by the skilled person as a function of the nature of the desired application The volume of the inner shell typically represents 0.1 to 99%, preferably 0.1 to 80% of the total volume of the shell.

The final composite membrane properties depend on multiple factors such as the concentration of the polyisocyanate within the capsule core. The initial thickness of the capsule membrane also affects the final composite membrane properties. The concentration of the polyisocyanate is adjusted to ensure that the concentration of the free polyisocyanate in the final product is below safety requirement.

Another object of the present invention is a perfuming composition comprising
(i) microcapsule slurry as defined in the present invention;
(ii) at least one ingredient selected from the group consisting of a perfumery carrier and a perfumery co-ingredient; and
(iii) optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsules as defined above.

The microcapsules of the present invention have multiple uses. For example, the microcapsules of the invention can be included in perfumery applications where capsules made by coacervation or by interfacial polymerization can be used, including but not limited to, consumer products such as, body wash, body care, air care and fine fragrances. In one embodiment, capsules with strong adhesive properties, are preferred. The presence of the coacervate component of the shell formed by the protein and the weakly anionic polyelectrolyte provides outstanding adhesive properties to the capsules of this invention.

The microcapsules of the invention described herein can be used as perfuming ingredients in consumer products of the home- or personal-care type.

Indeed, microcapsules according to the invention, although prepared with a simplified process, and in particular in the absence of a reactant being an amine or a polyamine to polymerize with the polyisocyanate, exhibit a good stability even in consumer products containing high amounts (typically more than 10% of their own weight) of specific type of surfactant/tensioactive/solvents which are known to significantly diminish the stability and the performance of other similar prior art capsules.

The use of the microcapsules disclosed herein provides a satisfactory stability in a chemically aggressive environment. In other words, the use of the capsules in various applications provides unforeseeable advantages over the same use of other similar prior art capsules.

The present invention also relates to the use of such microcapsules or perfuming composition in a consumer product that is preferably in the form of a home- or personal-care product. Such products may be either a solid or a liquid product. According to a particular embodiment, liquid products are preferred. The expression "home- or personal-care" has here the usual meaning in the art, and in particular, it includes products such as body-care, hair-care or home-care products. Examples of liquid products according to the invention may be selected from the group consisting of a shampoo or a hair conditioner, a liquid detergent, a fabric softener, a shower or bath mousse, oil or gel, a deodorant or an antiperspirant. Preferably, the liquid perfumed product is a shower gel, shampoo, a liquid detergent or a fabric softener. Examples of solid products according to the invention may be selected from the group consisting of a soap bar, a powder detergent or an air-freshener. As detergent products, there are considered applications such as detergent compositions or cleaning products for washing up or for cleaning various surfaces, for example, intended for textiles, dishes or hard surfaces (floors, tiles, stone-floors, etc). Preferably, the surface is a textile.

Conveniently, the microcapsules of the invention may be used as such to perfume the consumer products. For example, the microcapsules may be directly added to a consumer product in an amount of 0.1-30 wt. %, e.g. resulting in a total perfume content of about 0.0333-10 wt. %. Preferably, a consumer product according to the invention comprises about 0.01 to 4 wt. %, or even 4.5%, of its own weight, in capsules as defined above and containing the perfume oil ingredients. Of course, the above concentration may be adapted according to the olfactive effect desired in each product.

The invention also provides consumer products such as a laundry and cleaning composition comprising microcapsules of the invention and a detersive ingredient. Preferably, the laundry and cleaning composition is selected from the group consisting of a detergent composition, a hard surface cleaning composition, and a dishwashing composition. The invention also provides a process for making such laundry and cleaning composition, which comprises the step of combining the microcapsules of the invention, by means selected from spraying, dry-mixing, and mixtures thereof, with the detersive ingredient.

Most preferably, the laundry and cleaning composition is a fabric detergent or softener composition. Typical examples of fabric detergent or softener composition into which the microcapsules of the invention can be incorporated are described in WO 97/34986 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The process of the invention is therefore a cost effective solution to provide robust and stable microcaspules comprising a hydrogel shell (coacervate) that improves the adhesion and the mechanical properties of the capsule and an inner shell (polyurea) that provides additional and superior barrier properties.

Microcapsules obtained by the process of the invention exhibit excellent resistance against evaporation of the active agent when the capsules are in the dry state as well as excellent resistance against destabilization of the capsules in harsh environments, e.g., in detergent or surfactant solutions.

Depending on the safety status of the final product, the microcapsule of the invention may also be used in food applications where capsules made by coacervation are commonly used.

The invention will now be further described by way of examples. It will be appreciated that the invention as claimed is not intended to be limited in any way by these examples.

EXAMPLES

Example 1

Composite Polyurea/Coacervate Capsules Cross-Linked with Glutaraldehyde: Capsule X1 According to the Invention (No Amine or Polyamine is Added During the Process)

Aqueous solutions of 10% wt. pork gelatine (A) (250 Bloom, supplied by Norland), and 15% wt. gum Arabic (B) (Efficacia®, from CNI) are prepared separately.

A fragrance to be encapsulated is mixed with 10% of poly-isocyanate (trimethylol propane-adduct of xylylene diisocyanate, Takenate® D-110N, Mitsui Chemical) (C).

In a vessel at 40° C., 31.8 g of solution (A) and 21.2 g of solution (B) are added to 165.3 g of warm demineralised water under mechanical shear. pH is adjusted to 4.5 using HCl 1M. The mixture is maintained at 40° C. during 15 min.

31.8 g of solution (C) is slowly added to the mixture and homogenised at 230 RPM during 5 min, so as to reach an average droplet size of 600 µm. Mechanical shear is maintained while the solution is let to cool down at 10° C. at a rate of between 0.2 and 0.3° C.min-1. The stirring speed is slightly decreased, and 0.102 g of glutaraldehyde (aq. 50% wt. Supplied by Sigma-Aldrich) is added to the mixture. The capsule suspension is mixed during 4 to 10 hours at 20-25° C.

The result is an aqueous suspension or slurry of microcapsules.

Example 2

Composite Polyurea/Coacervate Capsules Cross-Linked with Glutaraldehyde: Capsule X1' According to the Invention (No Amine or Polyamine is Added During the Process)

Aqueous solutions of 10% wt. pork gelatine (A) (250 Bloom, supplied by Norland), and 15% wt. gum Arabic (B) (Efficacia®, from CNI) are prepared separately.

The fragrance to be encapsulated is mixed with 8% of poly-isocyanate (trimethylol propane-adduct of xylylene diisocyanate, Takenate® D-110N, Mitsui Chemical) (C).

In a vessel at 40° C., 29.2 g of solution (A) and 14.4 g of solution (B) are added to 130.9 g of warm demineralised water under mechanical shear. pH is adjusted to 4.55 using HCl 1M. The mixture is maintained at 40° C. during 15 min.

25.4 g of solution (C) is slowly added to the mixture and homogenised at 230 RPM during 5 min, so as to reach an average droplet size of 600 μm. Mechanical shear is maintained while the solution is let to cool down at 10° C. at a rate of between 0.2 and 0.3° C.min-1. The stirring speed is slightly decreased, and 0.102 g of glutaraldehyde (aq. 50% wt. Supplied by Sigma-Aldrich) is added to the mixture. The capsule suspension is mixed during 4 to 10 hours at 20-25° C.

The result is an aqueous suspension or slurry of microcapsules.

Comparative Example 3

Multilayered Polyurea/Coacervate Capsules Cross-Linked with Glutaraldehyde: Control Capsule X2 Using an Amine During the Process Aqueous solutions of (A) 10% wt. pork gelatine (250 Bloom, supplied by Norland); and (B) 10% wt. gum arabic (EFFICACIA®, from CNI); and (C) 3% wt. guanazol are prepared separately. A fragrance component to be encapsulated is mixed with (D) 8% of isocyanate (trimethylol propane-adduct of toluene diisocyanate, Desmodur® N4; origin: Bayer Material Science).

In a vessel at 40° C., 25.4 g of solution (A) and 12.7 g of solution (B) are added to 92.8 g of warm demineralised water under mechanical shear. The pH is adjusted to 4.5 using HCl 1M. The mixture is maintained at 40° C. for 15 min and then cooled down to 35-31° C. at a rate of 0.5° C.min$^{-1}$.

19.1 g of solution (D) is slowly added to the mixture and homogenised at 250 RPM for a period of 5 min, so as to reach an average droplet size of 600 μm. Mechanical shear is maintained while the solution is let to cool down at 10° C. at a rate of 0.5° C.min$^{-1}$. The stirring speed is then slightly decreased, and 0.102 g of glutaraldehyde (aq. 50% wt. Supplied by Sigma-Aldrich) is added to the mixture. Cross-linking is allowed to proceed for 4 to 10 hours at 20° C.

20 g of solution (C) is then added to the aqueous suspension of microcapsules at a rate of 1 ml/min. The mixture is kept under agitation for 1 to 4 hours at room temperature or optionally heated to temperature between 40-70° C.

The result is an aqueous suspension or slurry of capsules with composite polyurea/coacervate shells, the coacervate component being formed by gelatin and gum arabic.

Example 4

Stability in a Shower Gel Application

The stability of coacervated capsules, prepared according to example 3 (X2) and the hydrogel/polyurea capsules of the invention prepared according to examples 1 and 2 (X1 and X1') was compared in a shower gel. The model shower gel base used was composed of 50% deionized water, 5% thickener (acrylates/beheneth-25 methacrylate copolymer, available from Lubrizol), 43% surfactants (sodium pareth sulfate and cocamidopropyl betaine), 0.5% preservative (sodium benzoate); sodium hydroxide and citric acid are used to adjust the pH value.

Figure 2:
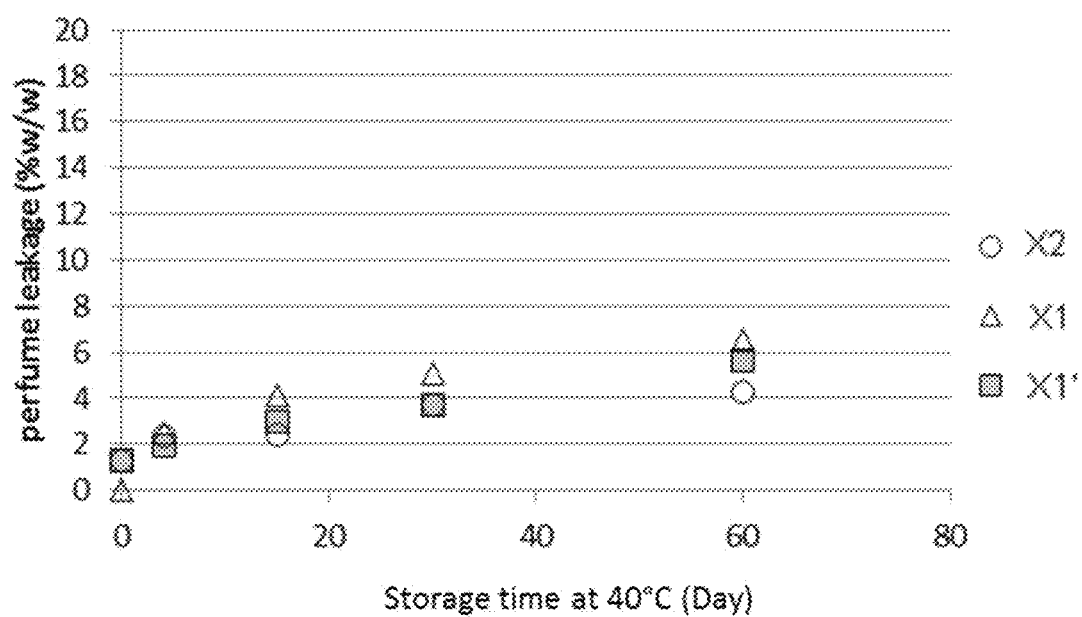
FIG. 2 is a graph showing the oil leakage as a function of storage time at 40° C.

The control capsules (X2) contained the same active agent as in the internal phase of the hydrogel/polyurea capsules according to the invention. As shown in FIG. 2, the hydrogel/polyurea capsules prepared as described in Examples 1 and 2 (i.e without using an amine) are as stable as the control coacervated capsules prepared by using an amine. This result demonstrates that suprisingly the absence of an amine during the process does not affect the stability of the capsules when subjected to highly concentrated surfactant media.

Thus, the present invention provides an optimized process that is not only cost effective but also that is not time consuming.

The invention claimed is:

1. A process for making a core-composite shell microcapsules slurry, which comprises:
   (i) providing as a dispersion in an aqueous vehicle, a hydrophobic internal phase comprising at least one polyisocyanate having at least three isocyanate functional groups and a hydrophobic active ingredient;
   (ii) mixing a first and second polyelectrolytes in the aqueous vehicle under conditions sufficient to form a suspension of complex coacervate nodules;
   (iii) depositing the complex coacervate nodules at an interface of the aqueous vehicle adjacent to the hydrophobic internal phase to form an outer shell of microcapsule, wherein the hydrophobic internal phase forms the core and contains the polyisocyanate and the hydrophobic active ingredient therein;
   (iv) providing conditions sufficient to induce interfacial polymerization of the polyisocyanate inside the outer shell to form an inner shell at the interface between the internal phase and the outer shell to form a core-composite shell microcapsule slurry; and
   (v) crosslinking the core-composite shell microcapsule slurry,
   wherein no amine or polyamine susceptible to polymerize with the polyisocyanate to form the inner shell is added at any stage of the process;
   wherein the pH of the microcapsule slurry obtained in step (iv) is not adjusted above 7.

2. The process according to claim 1, wherein no amount of other water-soluble reactant than an amine or polyamine susceptible to polymerize with the polyisocyanate is added at any stage of the process, the water-soluble reactant being chosen in the group consisting of polyols, thiols, ureas, urethanes, and mixtures thereof.

3. The process according to claim 1, wherein the first polyelectrolyte is gelatin and the second polyelectrolyte is selected from the group consisting of carboxymethyl cellulose, sodium carboxymethyl guar gum, xanthan gum and plant gums.

4. The process according to claim 3, wherein the second polyelectrolyte is acacia gum.

5. The process according to claim 1, wherein the at least one polyisocyanate having at least three isocyanate functional groups is present in an amount comprised between 0.1 and 30 wt % of the hydrophobic internal phase.

6. The process according to claim 1, wherein the at least one polyisocyanate having at least three isocyanate functional groups is an aromatic polyisocyanate.

7. The process according claim 1, wherein the hydrophobic active ingredient is selected from the group consisting of a perfume, a flavor, nutraceuticals, cosmetics, insect control agents, biocide actives and mixtures thereof.

8. A process for making a core-composite shell microcapsules slurry, which comprises:
   (i) providing as a dispersion in an aqueous vehicle, a hydrophobic internal phase comprising at least one polyisocyanate having at least three isocyanate functional groups and a hydrophobic active ingredient;
   (ii) mixing a first and second polyelectrolytes in the aqueous vehicle under conditions sufficient to form a suspension of complex coacervate nodules;
   (iii) depositing the complex coacervate nodules at an interface of the aqueous vehicle adjacent to the hydrophobic internal phase to form an outer shell of microcapsule, wherein the hydrophobic internal phase forms the core and contains the polyisocyanate and the hydrophobic active ingredient therein;
   (iv) providing conditions sufficient to induce interfacial polymerization of the polyisocyanate inside the outer shell to form an inner shell at the interface between the internal phase and the outer shell to form a core-composite shell microcapsule slurry; and
   a further step of drying the slurry obtained in step (iv) to obtain dried core-composite shell microcapsules;
   wherein no amine or polyamine susceptible to polymerize with the polyisocyanate to form the inner shell is added at any stage of the process;
   wherein the pH of the microcapsule slurry obtained in step (iv) is not adjusted above 7.

9. A core-composite shell microcapsule slurry obtained by the process of claim 1, wherein the inner shell consists essentially of polymerised polyisocyanate formed from at least one polyisocyanate comprising at least three isocyanate functional groups in the absence of a reactant consisting of a polyamine or an amine.

10. A consumer product in the form of a home- or personal-care product, in liquid or powder form, comprising from 0.1 to 50% by weight of surfactant, and core-composite shell microcapsules comprising an outer shell of a coacervate, an inner shell consisting essentially of polymerised polyisocyanate formed from at least one polyisocyanate comprising at least three isocyanate functional groups in the absence of a reactant consisting of a polyamine or an amine, and an internal phase comprising an hydrophobic active ingredient, wherein the inner shell and outer shell form a composite structure, and wherein the composite structure is crosslinked.

11. A perfuming composition comprising
   (i) a core-composite shell microcapsule slurry obtained by a process comprising:
      (i) providing as a dispersion in an aqueous vehicle, a hydrophobic internal phase comprising at least one polyisocyanate having at least three isocyanate functional groups and a hydrophobic active ingredient;
      (ii) mixing a first and second polyelectrolytes in the aqueous vehicle under conditions sufficient to form a suspension of complex coacervate nodules;
      (iii) depositing the complex coacervate nodules at an interface of the aqueous vehicle adjacent to the hydrophobic internal phase to form an outer shell of microcapsule, wherein the hydrophobic internal phase forms the core and contains the polyisocyanate and the hydrophobic active ingredient therein; and
      (iv) providing conditions sufficient to induce interfacial polymerization of the polyisocyanate inside the outer shell to form an inner shell at the interface between the internal phase and the outer shell to form a core-composite shell microcapsule slurry;
      wherein no amine or polyamine susceptible to polymerize with the polyisocyanate to form the inner shell is added at any stage of the process;
      wherein the pH of the microcapsule slurry obtained in step (iv) is not adjusted above 7;
      wherein the inner shell consists essentially of polymerised polyisocyanate formed from at least one polyisocyanate comprising at least three isocyanate functional groups in the absence of a reactant consisting of a polyamine or an amine, wherein the hydrophobic active ingredient comprises a perfume;
   (ii) at least one ingredient selected from the group consisting of a perfumery carrier and a perfumery co-ingredient; and
   (iii) optionally at least one perfumery adjuvant.

12. A consumer product in the form of a home- or personal-care product that includes a core-composite shell microcapsule slurry obtained by a process comprising:
   (i) providing as a dispersion in an aqueous vehicle, a hydrophobic internal phase comprising at least one polyisocyanate having at least three isocyanate functional groups and a hydrophobic active ingredient;
   (ii) mixing a first and second polyelectrolytes in the aqueous vehicle under conditions sufficient to form a suspension of complex coacervate nodules;
   (iii) depositing the complex coacervate nodules at an interface of the aqueous vehicle adjacent to the hydrophobic internal phase to form an outer shell of microcapsule, wherein the hydrophobic internal phase forms the core and contains the polyisocyanate and the hydrophobic active ingredient therein; and
   (iv) providing conditions sufficient to induce interfacial polymerization of the polyisocyanate inside the outer shell to form an inner shell at the interface between the internal phase and the outer shell to form a core-composite shell microcapsule slurry;
   wherein no amine or polyamine susceptible to polymerize with the polyisocyanate to form the inner shell is added at any stage of the process;
   wherein the pH of the microcapsule slurry obtained in step (iv) is not adjusted above 7;
wherein the inner shell consists essentially of polymerised polyisocyanate formed from at least one polyisocyanate comprising at least three isocyanate functional groups in the absence of a reactant consisting of a polyamine or an amine, in liquid or powder form in the form of a detergent composition, a fabric softener, a hard surface cleaning composition, a dishwashing composition, a shampoo, a hair conditioner, a shower or bath mousse, oil or gel, a deodorant, or an antiperspirant.

13. The consumer product according to claim 12, comprising from 0.1 to 50% by weight of surfactant.

14. Core-composite shell microcapsules obtained by the process of claim 8, wherein the inner shell consists essentially of polymerised polyisocyanate formed from at least one polyisocyanate comprising at least three isocyanate functional groups in the absence of a reactant consisting of a polyamine or an amine.

15. A perfuming composition comprising
   (i) core-composite shell microcapsules comprising an outer shell of a coacervate, an inner shell consisting essentially of polymerised polyisocyanate formed from at least one polyisocyanate comprising at least three isocyanate functional groups in the absence of a reactant consisting of a polyamine or an amine, and an internal phase comprising an hydrophobic active ingredient, wherein the inner shell and outer shell form a composite structure, and wherein the composite structure is crosslinked, wherein the hydrophobic active ingredient comprises a perfume;
   (ii) at least one ingredient selected from the group consisting of a perfumery carrier and a perfumery co-ingredient; and
   (iv) optionally at least one perfumery adjuvant.

16. The consumer product according to claim 10 in the form of a detergent composition, a fabric softener, a hard surface cleaning composition, a dishwashing composition, a shampoo, a hair conditioner, a shower or bath mousse, oil or gel, a deodorant, or an antiperspirant.

17. A consumer product in the form of a home- or personal-care product that includes the perfuming composition according to claim 11 as a detergent composition, a fabric softener, a hard surface cleaning composition, a dishwashing composition, a shampoo, a hair conditioner, a shower or bath mousse, oil or gel, a deodorant, or an antiperspirant.

* * * * *